US007067120B2

(12) United States Patent
Dianwen et al.

(10) Patent No.: US 7,067,120 B2
(45) Date of Patent: Jun. 27, 2006

(54) CYTOKINE GENE MODIFIED ANTIGEN-PRESENTING CELL/TUMOR CELL CONJUGATE, ITS PREPARATION AND USE

(75) Inventors: Ju Dianwen, Shanghai (CN); Qun Tao, Shanghai (CN); Dan Ye, Shanghai (CN)

(73) Assignee: Shanghai Medipharm Biotech Co., Ltd., Shanghai (CN)

( * ) Notice: Subject to any disclaimer, the term of this patent is extended or adjusted under 35 U.S.C. 154(b) by 0 days.

(21) Appl. No.: 10/106,173

(22) Filed: Mar. 25, 2002

(65) Prior Publication Data

US 2002/0182194 A1 Dec. 5, 2002

(30) Foreign Application Priority Data

Apr. 4, 2001 (CN) .............................. 01 1 05852

(51) Int. Cl.
  A61K 48/00 (2006.01)
  A01N 63/00 (2006.01)
  C12N 5/00 (2006.01)
  C12N 15/74 (2006.01)
  C12N 15/09 (2006.01)

(52) U.S. Cl. ................. 424/93.21; 424/93.1; 424/93.2; 435/325; 435/346; 435/455; 435/320.1; 435/373

(58) Field of Classification Search ................ 435/325, 435/455, 320.1, 373, 346; 424/93.2, 93.21
  See application file for complete search history.

(56) References Cited

U.S. PATENT DOCUMENTS

2002/0168351 A1* 11/2002 Ohno ....................... 424/93.21

OTHER PUBLICATIONS

Virgule: Dictionary.com*
Nishioka et al, Cancer Res 1999;59:4035-41.*
Osaki et al, Gene Ther 1999;6:808-15.*
Tanaka et al, Cancer Res. 2000;60:4838-44.*
"IFN-γ-Dependent and -Independent Mechanisms in Adverse Effects Caused by Concomitant Administration of IL-18 and IL-12", by Nakamura et al. The Journal of Immunology. 2000. 164: 3330-3336.

"Interleukin-12 and Interleukin-18 Synergistically Induce Murine Tumor Regression Which Involves Inhibition of Angiogenesis", by Coughlin et al. The American Society for Clinical Investigation. Inc., Antitumor Response of IL-12 and IL-18. vol. 101. No. 6. Mar. 1998. 1441-1452.
"Use of Peptide Libraries to Map the Substrate Specificity of a Peptide-Modifying Enzyme: A 13 Residue Consensus Peptide Specifies Biotinylation in *Escherichia coli*", by Peter J. Schatz. Bio/Technology vol. 11 Oct. 1993: 1138-1143.
"Phenotypic Analysis of Antigen-Specific T Lymphocytes", by Altman et al. Science. vol. 274. Oct. 4, 1996. pp. 94-96.
"Identification of Tyrosinase-related Protein 2 as a Tumor Rejection Antigen for the B16 Melanoma", by Bloom et al. The Journal of Experimental Medicine. vol. 185. No. 3. Feb. 3, 1997; 453-459.
"*In Vivo* Gene Therapy for α -Fetoprotein-producing Hepatocellular Carcinoma by Adenovirus-mediated Transfer of Cytosine Deaminase Gene", by Kanai et al. Cancer Research 57.461-465. Feb. 1, 1997.
"Dendritic Cells Retrovirally Transduced with a Model Antigen Gene Are Therapeutically Effective against Established Pulmonary Metastases", by Specht et al. The Journal of Experimental Medicine. vol. 186. No. 8. Oct. 20, 1997. 1213-1221.
"Cutting Edge: Physical Interaction Between Dendritic Cells and Tumor Cells Results in an Immunogen That Induces Protective and Therpeutic Tumor Rejection", by Celluzzi et al. The Journal of Immunology. vol. 18. 1998. pp. 3081-3085.
"Improved detection of nitric oxide radical (NO) production in an activated macrophage culture with a radical scavenger, carboxy PTIO, and Griess reagent", by F. Amano et al. FEBS Letters 368 (1995) 425-428.

(Continued)

*Primary Examiner*—Q. Janice Li
(74) *Attorney, Agent, or Firm*—Merchant & Gould P.C.

(57) ABSTRACT

The present invention provides an antigen-presenting cell (APC)/tumor cell conjugate, wherein the antigen-presenting cell (APC) is modified by a cytokine gene selected from the group consisting of IL-2, IL-3, IL-4, IL-6, IL-12, IL-18, IFNα, IFNβ, IFNγ, TNF, TGF, GM-CSE, and the combination thereof. The conjugate is useful as a tumor vaccine to significantly induce an immunity specifically against the tumor cell The present invention also provides the method for preparing the conjugate and a pharmaceutical composition containing said conjugate.

10 Claims, 11 Drawing Sheets

OTHER PUBLICATIONS

"Induction of Rapid T Cell Activation and Tolerance by Systemic Presentation of an Orally Administered Antigen", by Gütgemann et al. Immunity. vol. 8. 667-673. Jun. 1998.

"Frequency of Class I HLA-Restricted Anti-HIV CD8+ T Cells in Individuals Receiving Highly Active Antiretroviral Therapy (HAART)", by Gray et al. The Journal of Immunology. vol. 21. 1999. pp. 1780-1788.

"Recombinant modified vaccinia virus Ankara-simian immunodeficiency virus gag pol elicits cytotoxic T lymphcytes in rhesus monkeys detected by a major histocompatibility complex class I/peptide tetramer", by Seth et al. Proc. Natl. Acad. Sci. USA. vol. 95. pp. 10112-10116. Aug. 1998. Medical Sciences.

"Isolation of High Avidity Melanoma-Reactive CTL from Heterogeneous Populations Using Peptide MHC Tetramers", by Yee et al. The Journal of Immunology. vol. 23. 1999. pp. 2227-2234.

"The $\alpha_2$ Domain of H-2D$^4$ Restricts the Allelic Specificity of the Murine NK Cell Inhibitory Receptor Ly-49A", by Sundbäck et al. The Journal of Immunology. vol. 24. 1998. pp. 5971-5978.

T Helper Cell Type 1-associated and Cytotoxic T Lymphocyte-mediated Tumor Immunity Is Impaired in Interleukin 4-deficient mice, by Schuler et al. The Journal of Experimental Medicine. vol. 189. No. 5. Mar. 1, 1999: 803-810.

Interleukin 18 Transfection Enhances Antitumor Immunity Induced by Dendrtic Cell-Tumor Cell Conjugates, by Ju et al. Cancer Research 61. 3735-3740. May 1, 2001.

"Therapeutic Vaccination for Cancer", by Drew M. Pardoll. Clinical Immunology, vol. 95. No. 1. Apr. pp. S44-S62, 2000.

"Abrogation of Tumorigenicity and Metastasis of Murine and Human Tumor Cells by Transfection with the Murine IFN-$\beta$ Gene: Possible Role of Nitric Oxide", by Xie et al. Clinical Cancer Research, vol. 3 2283-2294. Dec. 1997.

"Dendritic Cells in Cancer Immunotherapy", by Fong et al. Annual Reviews, 2000 pp. 245-273.

"Murine dendritic cells pulsed *in vitro* with tumor antigen induce tumor resistance *in vivo*", by Flamand et al. Dendritic cells in immunotherapy. Eur. J. Immunol. 1994. 24:605-610.

"Peptide-pulsed Dendritic Cells Induce Antigen-specific, CTL-mediated Protective Tumor Immunity", by Celluzzi et al. J. Exp. Med., The Rockefeller University Press, vol. 183 Jan. 1996 283287.

"Murine dendritic cells-pulsed with whole tumor lysates mediate potent antitumor immune responses *in vitro* and*in vivo*", by Fields et al. Proc. Natl. Acad. Sci. USA. vol. 95. pp. 9482-9487. Aug. 1998, Immunology.

"Induction of Tumor Immunity and Cytotoxic T Lymphocyte Responses Using Dendritic Transfected with Messenger RNA Amplified from Tumor Cells", by Boczkowski et al. Cancer Research 60. 10284034. Feb. 15, 2000.

"In vivo antitumor effects of murine interferon-$\gamma$-inducing factor interleukin-18 in mice bearing syngeneic Meth A sarcoma malignant ascites", by Mieallef et al. Cancer Immunol Immunother (1997)43: 361-367.

"IFN-$\gamma$-Inducing Factor II -18 Administration Mediates IFN-$\gamma$-and IL-12-Independent Antitumor Effects", by Osaki et al. The Journal of Immunology. 1998. 160: 1742-1749.

\* cited by examiner

CYTOKINE GENE MODIFIED ANTIGEN-PRESENTING CELL/TUMOR CELL CONJUGATE, ITS PREPARATION AND USE

FIELD OF THE INVENTION

The present invention relates generally to the field of tumor medicine. Specifically, the invention relates to an antigen-presenting cell/tumor cell conjugate, the method of preparation and the use thereof. The invention also relates to a pharmaceutical composition and vaccine composition containing said conjugate.

BACKGROUND

Given the tremendous success in vaccination against infectious diseases, using tumor cells as immunogens to induce anti-tumor immunity is an attractive strategy to combat various human cancers. However, tumor cells themselves are usually poor immunogen. Possible reasons include down regulation of MHC molecules, lack of costimulatory molecules and unable to process and present antigen on cell surface. Numerous efforts have been made to transfect tumor cells with cDNAs of MHC molecule, costimulatory molecules, or particular cytokines to increase their immunogenicity and promote immune response (1). It has also been shown that hybrid between tumor cells and antigen-presenting cells (APCs) can induce strong anti-tumor immunity. Although many of these strategies have yielded promising results in animal models, clinical trials in humans are generally disappointing.

Dendritic cells (DCs) are unique high-potent antigen-presenting cells and capable of sensitizing naive $CD4^+$ T cells and $CD8^+$ T cells. With isolation and bulk propagation of DCs in vitro being available, great efforts have been made to use DCs in various immunization strategies (3). Immunization with DCs pulsed with tumor antigens or antigen-driven peptides can generate tumor-specific immune responses and anti-tumor effects (4,5). Since only a limited number of tumor-associated or tumor-specific antigens have been identified and shown recognized by cytotoxic T lymphocytes (CTLs), tumor-derived protein extracts or RNA have been used as the source of antigen (6,7). An additional potential advantage for these types of strategies is that they might induce immune response against multiple epitopes of tumors. However, the antigen-presenting pathways under these situations and the efficiency in priming both $CD4^+$ and $CD8^+$ T cells remain unclear.

Interleukin 18 (IL-18) was initially identified as a cytokine that facilitates the production of interferon-$\gamma$ (IFN-$\gamma$) induced by endotoxin. It is an essential factor for IFN-$\gamma$ production in response to microbial agents, and can act together with IL-12 in promoting the generation of IFN-$\gamma$-producing Th1 cells. In IL-18-deficient mice, there are defects in generation of Th1 response. These results indicate that IL-18 plays an essential role in inducing Th1 response in vivo. Consistent with the notion that Th1 cells are involved in anti-tumor immunity, administrations of IL-18 with or without IL-12 have significant anti-tumor effects (8, 9). However, administration of IL-18 is associated with septic shock-like severe toxicity that prevents its application (10). Interestingly, it was found that immunization with tumor cells expressing IL-18 with or without IL-12 could generate stronger antitumor effect than immunization with un-transfected tumor cells (11), indicating that vaccine expressing IL-12 and IL-18 may be used in inducing anti-tumor immunity.

Therefore, it has long been needed in the art to develop an effective, specific tumor vaccine with little or no side effect.

SUMMARY OF THE INVENTION

In the first aspect, the present invention provides an antigen-presenting cell/tumor cell conjugate wherein the antigen-presenting cell (APC) is modified by a cytokine gene selected from the group consisting of IL-2, IL-3, IL-4, IL-6, IL-12, IL-18, IFN$\alpha$, IFN$\beta$, IFN$\gamma$, TNF, TGF, GM-CSF, and the combination thereof.

In the second aspect, the present invention provides a method for preparing the antigen-presenting cell/tumor cell conjugate comprising the steps of:
  (1) providing said antigen-presenting cell and tumor cell, wherein the antigen-presenting cell (APC) is modified by a cytokine gene selected from the group consisting of IL-2, IL-3, IL-4, IL-6, IL-12, IL-18, IFN$\alpha$, IFN$\beta$, IFN$\gamma$, TNF, TGF, GM-CSF, and the combination thereof;
  (2) incubating said APC and tumor cell with a ratio APC: tumor cell of 100:1–0.1:1 in the temperature of 30–38° C. for 1–100 hrs to form the antigen-presenting cell/ tumor cell conjugate.

In a preferred embodiment, the method further comprises the step of:
  (3) irradiating said conjugate with a dose of 1000–100,000 Rad or chemically inactivating the formed conjugate, e.g., by using mitomycin.

In the third aspect, the present invention provides a pharmaceutical composition comprising the antigen-presenting cell/tumor cell conjugate of the invention and the pharmaceutically acceptable carrier or excipient or adjuvant.

In a preferred embodiment, said pharmaceutical composition is a tumor vaccine.

In the fourth aspect, the present invention provides the use of the antigen-presenting cell/tumor cell conjugate of the invention, wherein it is used for the preparation of a medicine for the therapy of cancer or a vaccine for the prophylaxis of cancer.

A, Groups of mice (n=10) were immunized with irradiated DC-E.G7 vaccine, DC and E.G7 cell co-injection, peptide pulsed DC 14 and 7 days before challenging with E.G7 cells.

B, Anti-CD4, anti-CD8 ascites containing 0.1 mg of McAb were injected i. p. into each mice 4 and 1 days either before immunization or before challenging with tumors and another 3 injections of McAbs were performed at 3-day intervals.

C. Tumor protection in IFN-γ-R$^{-/-}$ or IL-4$^{-/-}$ mice immunized with DC-E.G7 vaccine or control vaccines.

Figure 4:
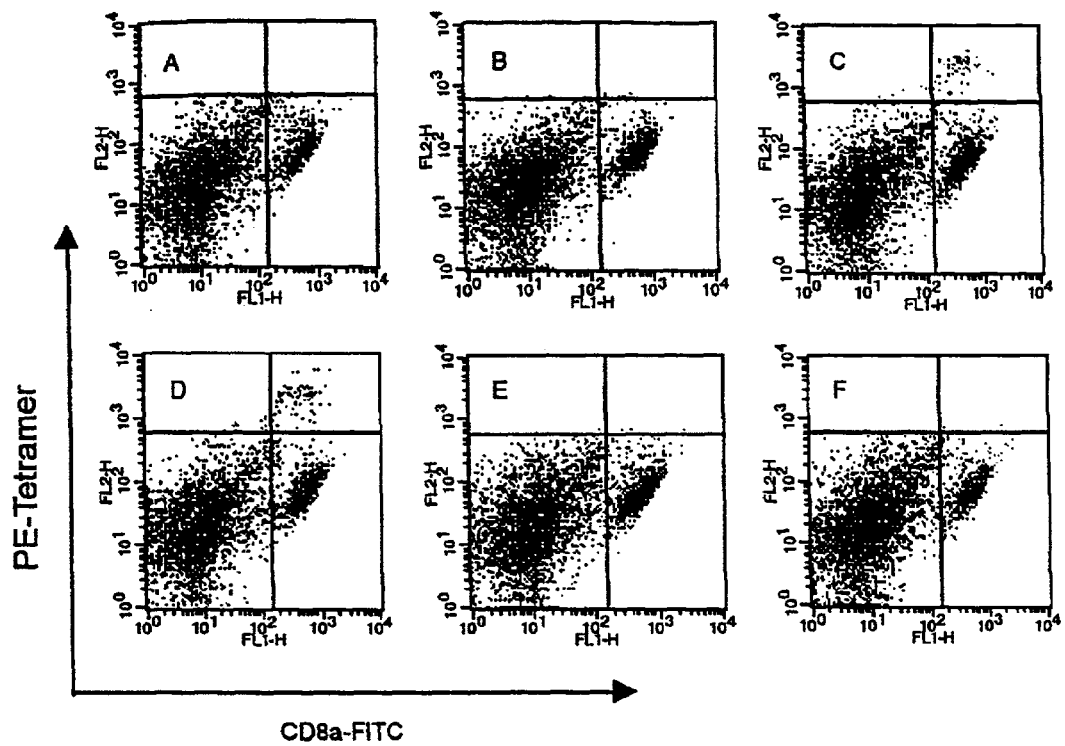
Figure 4:
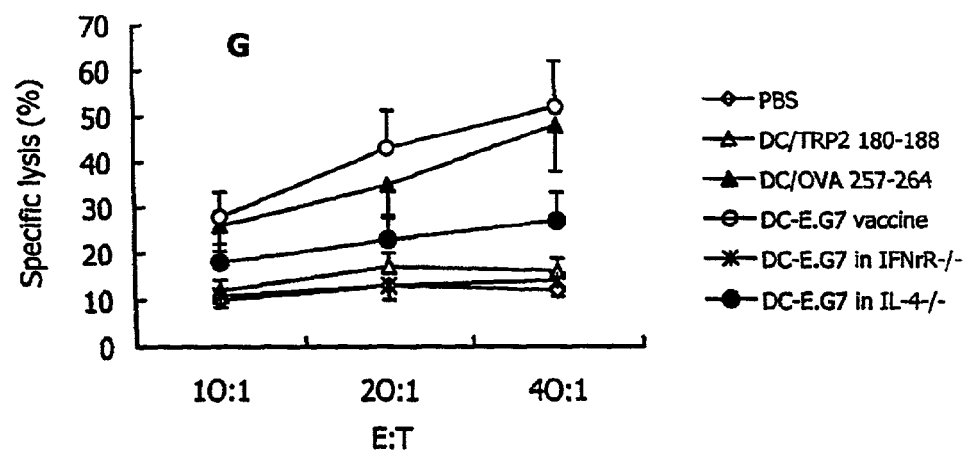

FIG. 4. Induction of tumor-specific CD8$^+$ T cells after immunization of mice with DC-E.G7 vaccine. A-F, Appearance of tetramer$^+$CD8$^+$ T cells in mice after treatments with PBS (A), TRP2$_{180-188}$ pulsed DC (B), OVA$_{257-264}$ pulsed DC (C), or DC-E.G7 vaccine (D) in wild type C57BL/6 mice, or after immunization with DC-E.G7 vaccine in IFN-γ-R$^{-/-}$ mice (E) and IL-4$^{-/-}$ mice (F). Lymphocytes were stained with PE-conjugated H-2K$^b$/OVA$_{257-264}$ tetramer and FITC-conjugated CD8a McAb. G, Tumor specific CTL cytotoxicity of lymphocytes derived from mice after different therapies. Cytotoxicity was determined by a standard 4-h $^{51}$Cr release assay by utilizing E.G7 cells as targets.

FIG. 5. Tumor weights in mice after immunotherapy with IL-18 gene modified DC-E.G7 cell vaccine.

A, Tumor-bearing mice (n=10 in each group) were treated with IL18DC-E.G7 vaccine, Lac Z gene-modified DC-E.G7 vaccine, DC-E.G7 vaccine, OVA$_{257-264}$ pulsed DC, IL-18 gene modified DC, DC alone or PBS.

B, Anti-CD4, anti-CD8, or antiNK1.1 ascites containing 0.1 mg of McAb were injected i. p. into each mice 4 and 1 days before tumor inoculation and another 3 injections of McAbs were performed 2, 5, 8 days after tumor inoculation.

C. Tumor weights in wild type, IFN-γ-R$^{-/-}$ or IL-4$^{-/-}$ mice received DC-E.G7 cell vaccine or control therapies.

Figure 6:
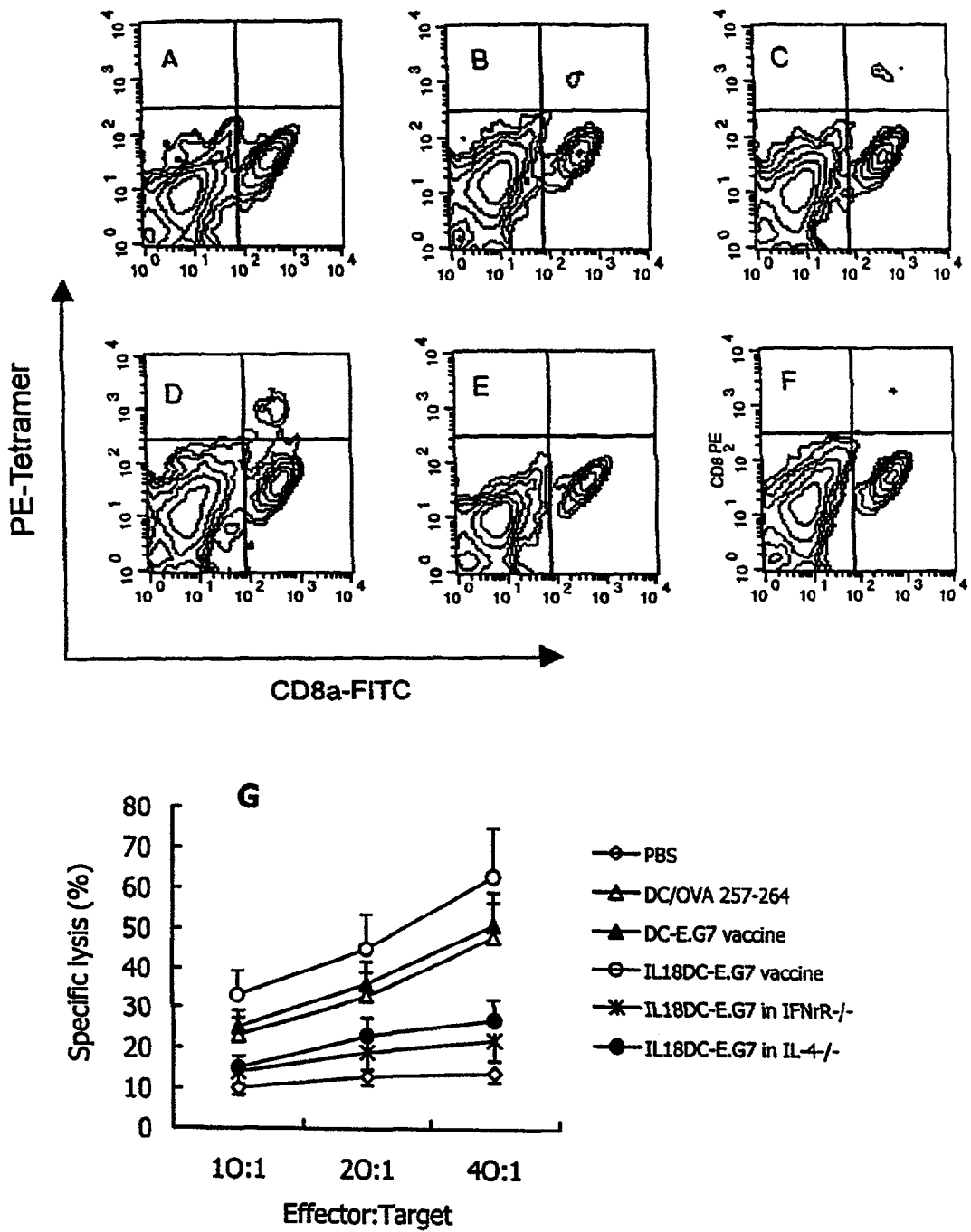
Figure 7A:
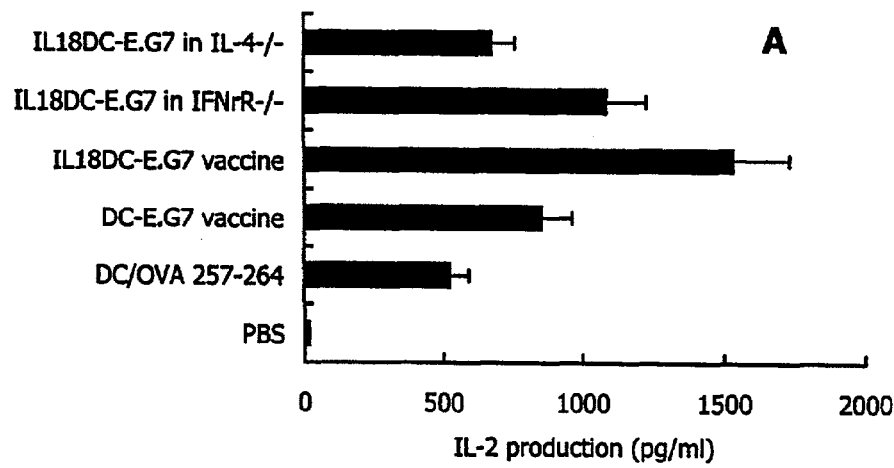
Figure 7B:
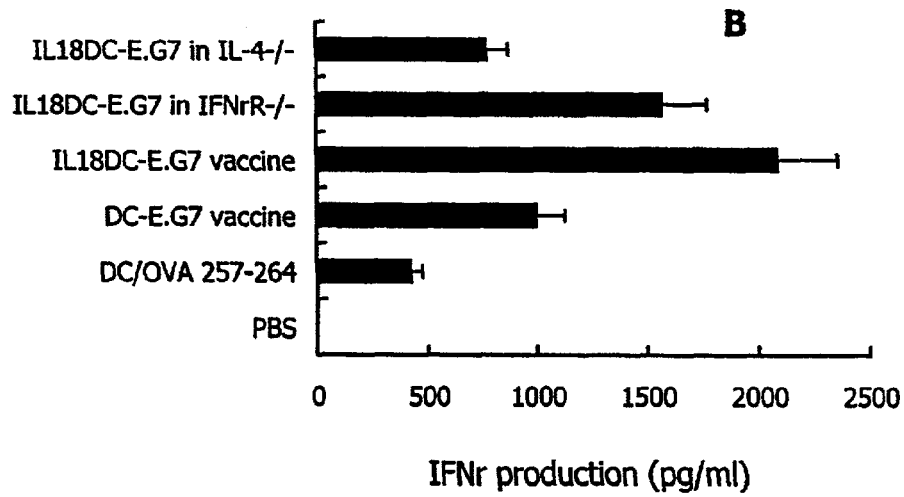
Figure 7C:
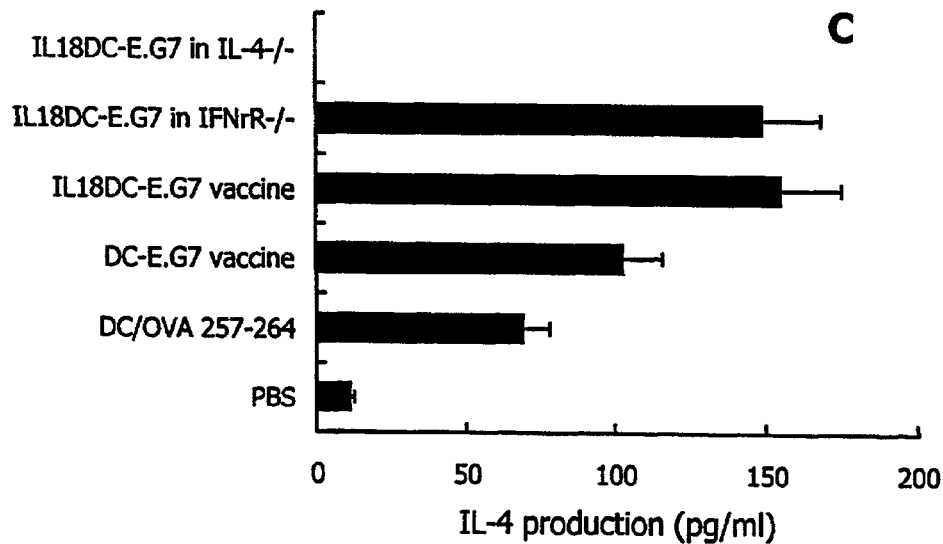
Figure 7D:
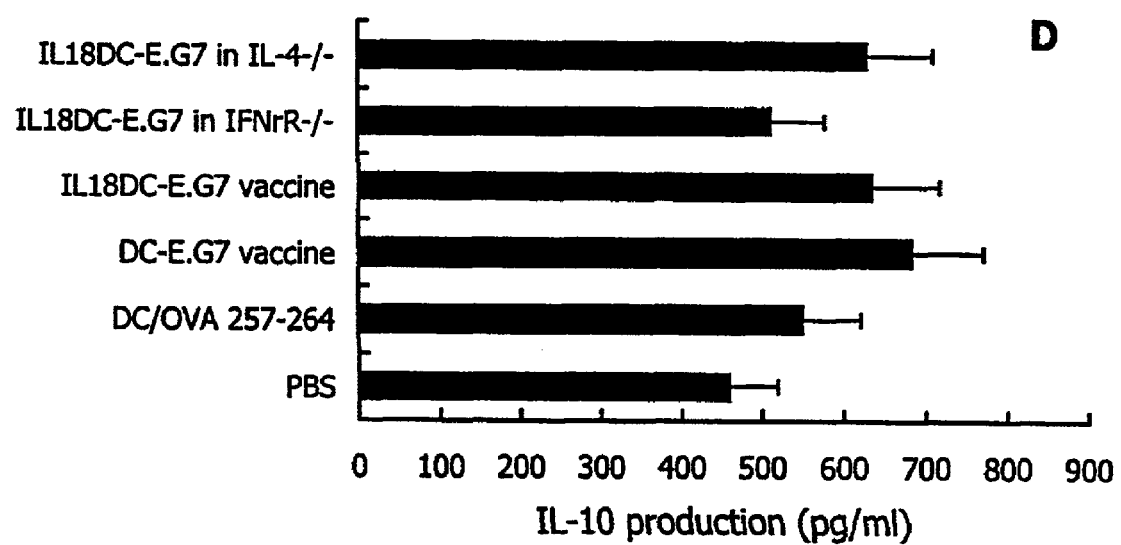

FIG. 6. Induction of tumor-specific CD8$^+$ T cells after immunotherapy of established tumors with IL18DC-E.G7 vaccine. A-F, Appearance of tetramer$^+$CD8$^+$ T cells in mice after treatments with PBS (A), OVA$_{257-264}$ pulsed DC (B), DC-E.G7 vaccine (C), or IL18DC-E.G7 vaccine (D) in wild type mice, or after treatments with IL18DC-E.G7 vaccine in IFN-γ-R$^{-/-}$ mice (E) and IL-4$^{-/-}$ mice (F), respectively. Lymphocytes were stained with PE-conjugated H-2K$^b$/OVA$_{257-264}$ tetramer and FITC-conjugated anti-CD8a McAb. G, Tumor specific CTL cytotoxicity of lymphocytes derived from mice after different therapies. Cytotoxicity was determined by a standard 4-h $^{51}$Cr release assay by utilizing E.G7 cells as targets.

FIG. 7. Production of cytokines by splenic lymphocytes in tumor-bearing mice after treatments with IL18DC-E.G7 vaccine, DC-E. 7 vaccine, OVA$_{257-264}$ pulsed DC, or PBS, or after treatments with IL18DC-E.G7 vaccine in CD4$^+$ T cell-depleted wild type mice, IFN-γ-R$^{-/-}$ mice and IL-4$^{-/-}$ mice, respectively. A, IL-2 production. B, IFN-γ production. C, IL-4 production. D, IL-10 production. The cytokine contents in the supernatants of lymphocytes after stimulation with irradiated E.G7 cells were determined with ELISA.

Figure 8A:
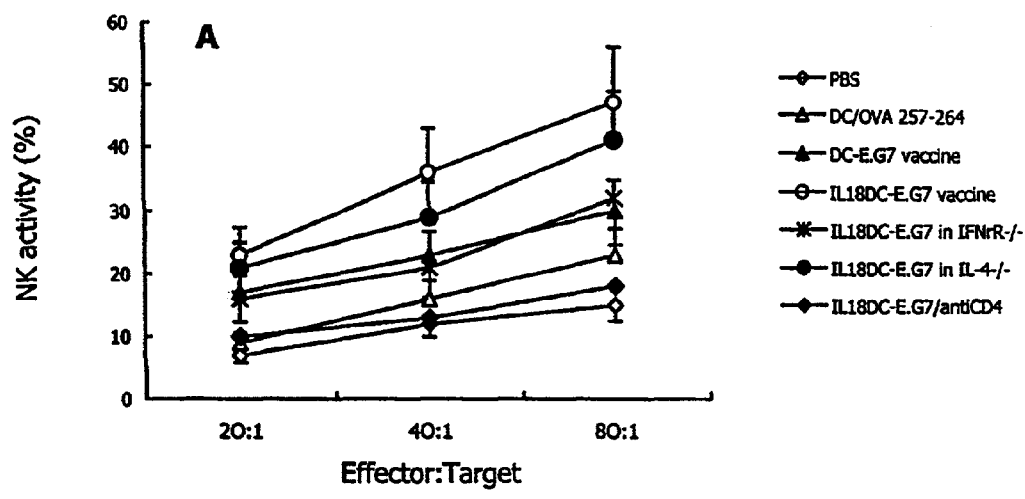
Figure 8B:
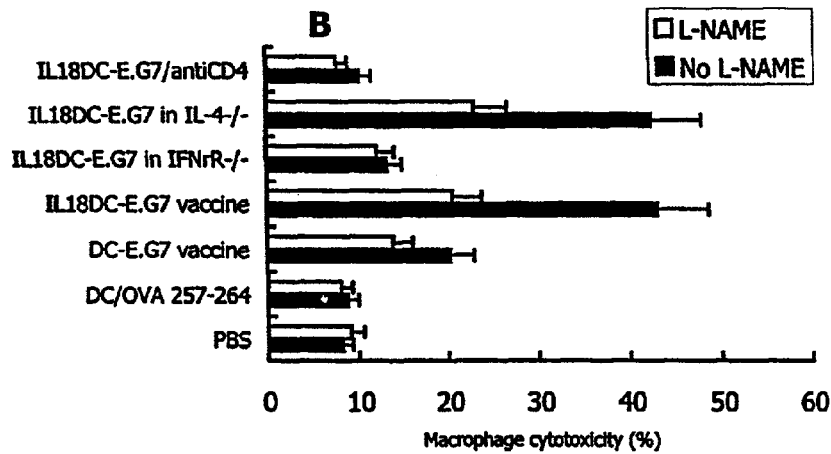
Figure 8C:
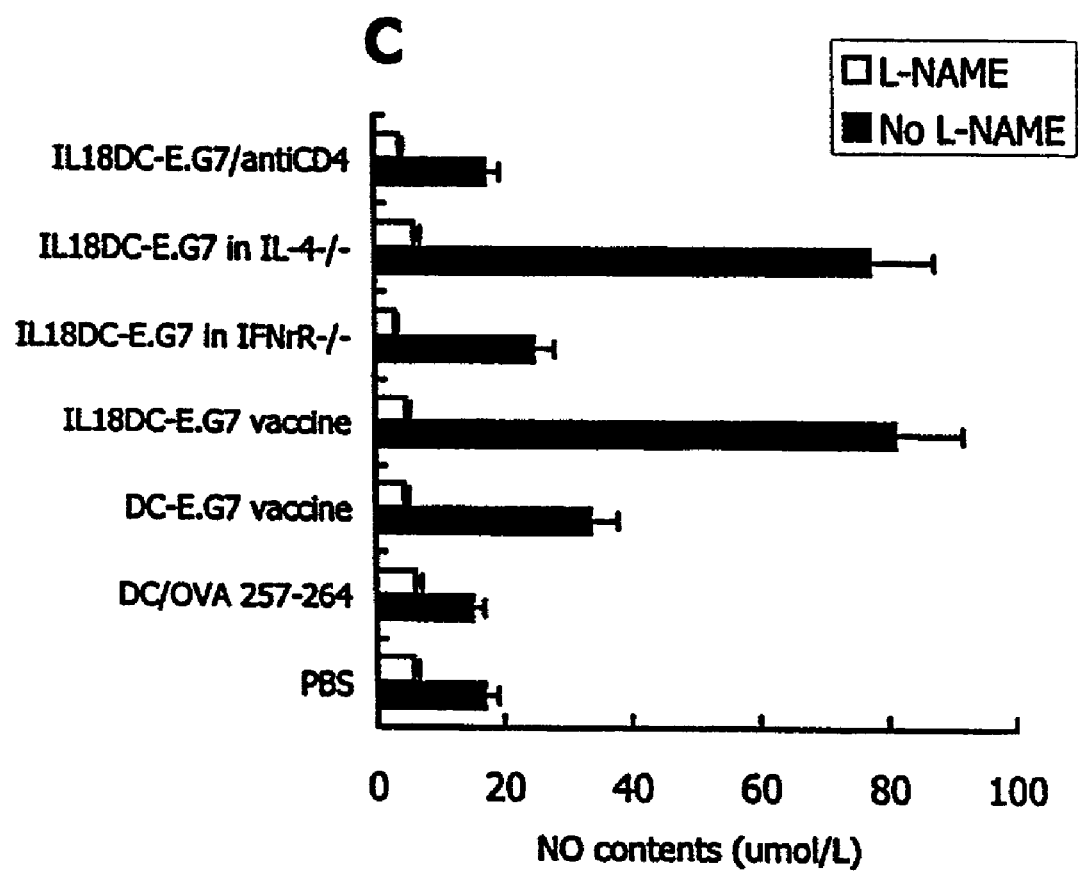

FIG. 8. Activation of non-specific antitumor immunity in CD4$^+$ T cell-dependent manner in tumor-bearing mice after treatment with IL18DC-E.G7 vaccine, DC-E.G7 vaccine, OVA$_{257-264}$ pulsed DC, or PBS, or after treatments with IL18DC-E.G7 vaccine in CD4$^+$ T cell-depleted wild type mice, IFN-γ-R$^{-/-}$ mice and IL-4$^{-/-}$ mice, respectively. A, NK activity determined by a standard 4-h $^{51}$Cr release assay by utilizing YAC-1 cells as targets. B, C, Cytotoxicity (B) and nitric oxide release (C) of splenic macrophages in the absence or presence of NO synthase inhibitor L-NAME. The cytotoxicity of macrophages was assayed using L1210 as target cells and NO contents assayed using Gress's reagent.

DETAILED DESCRIPTION OF THE INVENTION

As used herein, term "antigen-presenting cell (APC)/tumor cell conjugate" means a conjugate formed by contacting APC with tumor cell. Said term includes not only the conjugate formed by one APC with one or more tumor cell, but also the conjugate formed by one tumor cell with one or more APC. In fact, said term further includes the mixture of APC/tumor cell so long as at least 5%, preferably at least 20%, more preferably at least 50%, most preferably at least 75% APC exists in the form of conjugate, or was formed conjugate with tumor cells. In the present invention, during the formation of conjugate, it may or may not add a substance which facilitates the conjugation.

The APCs useful in the present invention have no special limitation. Suitable APCs include, but are not limited to, the following cells: dendritic cell, macrophage, B cell, endothelial cell, Langerhans cell, and combination thereof.

The tumor cell useful in the present invention has no special limitation. Suitable tumor cells include the fresh tumor cell isolated from the tumor tissue and the tumor cell line cultured in vitro. Preferably, said tumor cell is selected from, but is not limited to the cell of melanoma, kidney cancer, pulmonary carcinoma, hepatic carcinoma, mammary cancer, prostatic carcinoma, gastric carcinoma, and leukemia.

In the conjugate of the present invention conjugate, the ratio in molar of APC: tumor cell is about 100:1–0.1:1, preferably 10:1–1:1.

There is no special limitation to the cytokine used to modify APCs. The examplary cytokine includes, but is not limited to L-2, IL-3, IL-4, IL-6, IL-12, IL-18, IFNα, IFNβ, IFNγ, TNF, TGF, GM-CSF, and the combination thereof. Preferably, the cytokine is selected from IL-2, IL-3, IL-4, IL-6, IL-12, IL-18, IFNα, IFNβ, IFNγ, TNF and the combination thereof. More preferably, the cytokine is selected from IL-12, IL-18, IFNα, IFNβ, IFNγ and the combination thereof.

The cytokine gene can be introduced into APC by using various conventional technologies, e.g., using adenovirus, retrovirus, adeno-associated virus as a vector, or using non-virus vector, such as plasmid DNA, to carry out the transformation.

After obtaining the cytokine-modified APC and tumor cell, they can be incubated together in a suitable temperature to form conjugates. In one embodiment, the conjugates are formed by incubating APC and tumor cell at 30–38° C., preferably 35–37° C. for 1–100 hr, preferably 2–50 hr.

As to the tumor vaccine formed by conjugating APC and tumor cell, it is usually necessary for the tumor vaccine to be inactivated before administration to the human body. Of course, under some circumstances, the inactivation may not be necessary. The common methods of inactivation can be used in the present invention. Suitable methods include chemical inactivation, e.g., by mitomycin, and irradiation treatment. The dose for irradiation is usually from 1000 to 100,000 Rad, preferably 10,000–50,000 Rad.

The therapeutic efficacy and the capability of the conjugate of the present invention conjugate for inducing antigen-specific killing T cells can be measured by using a tetramer. A tetramer is composed of tumor-specific antigen polypeptide, MHC-I carrying biotin, microglobulin and avidin.

The APC/tumor cell conjugate of the present invention can be used for the preparation of a medicine for the therapy of cancer or a vaccine for the prophylaxis of cancer.

Pharmaceutical Compositions

Pharmaceutical compositions can comprise (include) a therapeutically effective amount of the conjugates of the invention and the pharmaceutically acceptable carrier, excipent, or adjuvant.

The term "therapeutically effective amount" as used herein refers to an amount of a therapeutic agent to treat, ameliorate, or prevent a desired disease or condition, or to exhibit a detectable therapeutic or preventive effect. The precise effective amount for a subject will depend on the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician.

For purposes of the present invention, an effective dose of conjugate will be $10^5$–$10^8$ APC per administration, and preferably $10^6$–$10^7$ APC per administration .

A pharmaceutical composition can also contain a pharmaceutically acceptable carrier. The term "pharmaceutically acceptable carrier" refers to a carrier for administration of a therapeutic agent. The term refers to any pharmaceutical carrier that does not itself induce the production of antibodies harmful to the individual receiving the composition, and which may be administered without undue toxicity. Suitable carriers may be large, slowly metabolized macromolecules, such as proteins, polysaccharides, polylactic acids, and polyglycolic acids. Such carriers are well known to those of ordinary skill in the art. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions, solid forms suitable for solution in, or suspension in, liquid vehicles prior to injection may also be prepared.

A particular pharmaceutical composition is tumor vaccine . The tumor vaccine of the present invention is a novel tumor vaccine, which significantly induces the CD4$^+$ T cell- and CD8$^+$ T cell- dependent anti-tumor immunity. This kind of tumor vaccine immunization can significantly induce antigen-specific CD8$^+$ T cells. The endogenous Th1 type cytokines, IFN-γ and Th2 type cytokines as well as IL-4 play an important role in the induction of anti-tumor immunity by the adhesive tumor vaccine.

The tumor vaccine of the present invention can be used not only for the treatment of various tumors, but also for the prevention from the recurrence and metastasis of tumor.

The tumor vaccine of the present invention can be used alone or in combination with radiotherapy, chemotherapy, surgery or other biological therapy, so as to achieve the best therapeutic or prophylactic effects.

Delivery Methods

Once formulated, the compositions of the invention can be administered directly to the subject. The subjects to be treated can be animals. In particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Dosage treatment may be a single dose schedule or a multiple dose schedule.

In one embodiment of the invention, a novel DC-based vaccine was prepared, which consists of DCs and EL4 cells transduced with cDNA of OVA. The immunization with DC-E.G7 conjugate resulted in formation of a Th1-cytokine-producing cells, antigen-specific CD8$^+$ T cells, and strong CD4$^+$/CD8$^+$ T cells-dependent anti-tumor immunity. To further improve the efficiency of vaccine, the DC transformed with IL-18 was used to prepare IL18DC-E.G7 conjugate. When immunized with this conjugate, it further significantly improved the number of Th1 cytokines and antigen-specific CD8$^+$ T cells, resulting in strong anti-tumor immunity.

The APC/tumor cell conjugate of the invention has the following advantages:

(1) High specificity. The induced anti-tumor immunity is only against the existing tumor cell and produce specific anti-tumor effect.

(2) Little side effect. The anti-tumor effect is aimed at tumor, resulting little side effect.

(3) Strong anti-tumor effect. The effect of anti-tumor of the invention is better than the non-modified conjugate, the DC only pulsed with polypeptide, or any other DC-based tumor vaccines in the art.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLES

MATERIALS AND METHODS

Animals and Cell Lines

Male or female wild type C57BL/6 (C57BL/6, H-2$^b$) mice, IL-4 gene knockout mice (IL-4$^{-/-}$) (C57BL/6), interferon-γ receptor gene knockout mice (IFN-γ-R$^{-/-}$) (C57BL/6), 6–8 weeks of age, provided by Joint Venture SIPPR-BK Experimental Animal Co. (Shanghai, China), were housed in specific pathogen free state for all experiments. MHC-II negative, H-2$^b$ T thymoma cells E.G7, produced by transfection of EL4 cells with cDNA encoding chicken egg OVA (provided by Dr. Gilboa E, Duke University), NK sensitive YAC-1 cells and 293 cells, a continuous cell line derived from human embryonic kidney, L1210 mouse leukemia cells, were maintained in RPMI-1640 medium supplemented with penicillin 100 U/ml, streptomycin 100 μg/ml, 2-mercaptoethanol 50 mM and 10% fetal calf serum (FCS). FCS and all culture media were purchased from Gibco-BRL, USA.

Example 1

Preparation of OVA-specific Tetramers

The DNA encoding a specific biotinanylation site with 14 amino acids (12, 13) was fused to the COOH terminus of cDNA of the non-transmembrane region (residues 1–280) of H-2K$^b$ heavy chain by using the upstream primer 5' CTA GCT AGC GGC CCA CAC TCG CTG AGG 3' (SEQ ID NO: 1) and downstream primer 5' CGC GGA TCC TTA ACG ATG ATT CCA CAC CAT TTT CTG TGC ATC CAG AAT ATG ATG CAG GGA TCC AGT GGA TGG AGG AGG CTC 3'(SEQ ID NO: 2). H-2K$^b$ expression plasmid pLKb 1.1, kind gift from Dr. Shields MJ, NCI, NIH, was subjected as template to 35 cycles of 94° C. for 1 min, 56° C. for 1 min 72° C. for 1 min, and a final 15 min at 72° C. using PCR beads (Amersham-Pharmacia, Piscataway, USA). The amplified PCR product was cut with Nhe I/BamH I restriction enzymes (New England Biolabs), gel-purified and ligated into pET21d vector (Novagen, Inc., Madison, Wis.) digested with Nhe I/BamH I. The fusion protein-expressing plasmid and pET3a harboring human β2-microglobulin (provided by Dr. Shields MJ, NCI, NIH) were transfected into E. coli BL21 (DE3) as an expression host.

The cells transformed with either fused H-2K$^b$- or P2-microglobulin-expressing plasmids were incubated at 37° C. and induced to produce protein by the addition of isopropyl β-D-thiogalactopysanoside (IPTG) at 0.1 mM. The harvested cells were re-suspended in 200 mM Tris-HCl, pH8.0, containing 2mM EDTA and incubated at 22° C. for 20 min, and then the cell pellets were lysed by sonication. The inclusion body was washed four times and dissolved in 6 M Guanidine-HCl containing 0.3 M DTT, 100 mM Tris-HCl, pH8.0, and a mixture of protease inhibitors. H-2K$^b$/peptide complexes were refolded by dilution. The peptides corresponding to the amino acid sequence of OVA residues 257–264 (SIINFEKL) (SEQ ID NO: 3)or of TRP2 residues 180–188 (SVYDFFVWL)(SEQ ID NO: 4) were obtained from Macromolecular Resource Facility, Colorado University, USA (14,15). These peptides were synthesized by solid phase techniques with free amino and carboxyl ends and purified by reverse phase HPLC and were >95% purity as determined by analytical HPLC. The peptides, dissolved in DMSO, H-2K$^b$ heavy chain and β2-microglobulin were refolded together over 72 h in 0.4 M arginine, 5 mM oxidized glutathoine, 100 mM Tris, 2 mM EDTA at 10° C. The refolded H-2K$^b$/peptide/p2-microglobulin complexes were purified by gel filtration over a Sephacryl S-200 column (Pharmacia, Sweden) in 20 mM Tris-HCl, pH8.0.

The purified complexes were biotinylated for 2 h at 25° C. in the presence of Biotin in 10 mM Tris-HCl, pH 7.5, containing Bir A enzyme 1 uM, NaCl at 150 mM, adenosine triphosphate at 5 mM, MgCl$_2$ at 5 mM (AVIDITY, Boulder, Colo., USA). The biotinylated complexes were further purified by gel filtration and the H-2K$^b$ tetramer was prepared by mixing of H-2K$^b$ and PE-conjugated streptavidin (Biosource, Camarillo Calif.) at a molar ratio of 4:1. The tetramer was then stored at 4° C. in PBS (pH7.4) at a concentration of 1 mg/ml in a cocktail containing 0.1 sodium azide, 1 ug/ml pepstatin, 1 ug/ml leupeptin and 1 ug/ml aprotinin.

Example 2

Recombinant Adenovirus Preparation

Replication-defective recombinant adenovirus AdlacZ encoding β-galactosidase, and AdIL18 encoding murine IL-18 were constructed from human adenovirus serotype 5 using homologous recombination. The expression of these genes was driven by CAG promoter (16). These adenoviruses were propagated in 293 cells and the titers of the adenovirus were determined with a standard plaque forming unit (PFU) assay.

Example 3

Preparation of bone marrow-derived DC

DCs were prepared from bone marrow as described previously with minor modifications. Briefly, erythrocyte-depleted bone marrow cells were re-suspended in RPMI-1640 media supplemented with recombinant murine GM-CSF (20 ng/ml, Genzyme Corp., Cambridge, Mass.) and IL-4 (20 ng/ml, Genzyme Corp., Cambridge, Mass.). Three days later, the adherent cells were re-suspended in new media supplemented with GM-SCF and IL-4. The loosely adherent cells were harvested as DC after another 3–4 days. These DCs expressed CD80, CD86, CD40, and Iab when analyzed by flow cytometry (data not shown).

Example 4

Pulsing of DC with OVA$_{257-264}$ peptides

For pulsing of DCs with peptides, the DCs were re-suspended in reduced serum media at 3×10$^6$ cells/ml and pulsed with OVA$_{257-264}$ peptides 10 ug/ml in the presence of human β2-microglobulin (Sigma Chemical Co. St. Louis, USA) 10 ug/ml for 3 h at 37° C. with gentle mixing every 30 min. The cells were then washed twice and re-suspended in PBS at 10$^6$ cells/ml (17).

Example 5

Preparation and Flow Cytometry Analysis of DC-E.G7 Cell Association

For the analysis of DC and tumor cell association, the E.G7 cells were labeled with PKH26 in Dilution C for 3 min at 25° C. as indicated by the instructions of the manufacturer (Sigma Chemical Co., St. Louis, Mo., USA). DCs were incubated with E.G7 tumor cells at a ratio of 6:1 for 6 h and 24 h to form stable DC-E.G7 conjugate (38). The DCs, in the presence or absence of PKH26-labeled EG. 7 cells, were labeled with FITC-conjugated anti-Ia$^b$ McAb (PharMingen, San Diego, USA) for 30 min at 4° C. in PBS supplemented with 2% FCS and 0.02% sodium azide followed by washing twice in the same PBS.

Example 6

Immunization with DC-E.G7 Vaccine

For immunization, DCs were incubated with E.G7 tumor cells at a ratio of 6:1 for 24 h to form stable DC-E.G7 conjugate and the conjugate was used as DC-E.G7 vaccine (18). The DC-E.G7 vaccine (10$^5$ of DC and 1.6×10$^4$ of E.G7 tumor cells, respectively), the same number of DCs and E.G7 cells mixture without incubation, and $10^5$ DCs pulsed with peptides after irradiation (3000 Rad), or PBS were injected s. c. into right flank region of C57BL/6 mice and the same immunization was boosted a week later. Tumor challenge was initiated by injecting of $10^5$ E.G7 cells s. c. into the rear leg of the immunized mice 1 week after the last immunization. Tumor occurrence was observed twice weekly and a tumor diameter of less than 0.5 cm was regarded as tumor free.

Example 7

Immunotherapy with IL-18 gene-modified DC-E.G7 Vaccine

For immunotherapy of established E.G7 tumors, tumor-bearing mice were established by s. c. inoculation of $10^5$ E.G7 cells. DCs were transfected with AdIL18 at a MOI of 10:1 for 12 h and then washed twice in RPMI-1640. Then the IL-18 gene-modified DCs were incubated with E.G7 cells at a ratio of 6:1 for 24 h to form stable IL18DC-E.G7 vaccine. The irradiated DC-E.G7 cell conjugate, AdLacZ gene modified DC-E.G7 vaccine, IL18 gene-modified DCs alone, DCs and E.G7 without incubation, or PBS were injected s. c. into the flank region of the tumor-bearing mice 3 days after tumor inoculation, and the same therapy was repeated 1 week later. The tumor-bearing mice were sacrificed 7 days after the second immunotherapy and tumor weights were determined.

Example 8 in vivo Depletion of Specific Cell Subsets

Monoclonal antibodies (McAbs) used to deplete cell subsets in vivo were prepared from the hybridomas GK1.5 (anti-CD4, ATCC TIB207), 2.43 (anti-CD8, ATCC TIB210), or PK136 (anti-NK1.1, ATCC HB-191). Ascites containing 0.1 mg of McAb in 0.1 ml PBS were injected i.p. into each mice 4 and 1 days either before immunization or inoculation of tumors, and another 3 injections of McAbs were performed at 3-day intervals. Flow cytometry analysis of splenocytes and peripheral blood cells revealed that more than 98% of the targeted cells were depleted.

Example 9

Staining of $CD8^+$ T Cells by Tetramer

For antigen-specific $CD8^+$ T cell analysis, non-adherent lymphocytes were incubated with $H-2K^b$/OVA or $H-2K^b$/TRP2 tetramers for 3 h. In the last 30 min of the incubation period, the FITC-conjugated anti-CD8a McAb (Biosource International, USA) was added for further incubation. Cells were analyzed on a Becton Dickinson FACS Flow Cytometer (Becton Dickinson, San Jose, Calif.). Data acquisition and analysis were performed using CellQuest software.

Example 10

Cytotoxic Assay of CTL and NK Cells

Splenic lymphocytes were isolated from sacrificed mice 14 or 17 days after tumor inoculation. The erythrocytes were depleted with 0.83% ammonium chloride and macrophages were removed by adherence of splenocytes on plastic plates for 2 h. The non-adherent lymphocytes were used as NK effector cells. The lymphocytes were co-cultured with inactivated E.G7 cells (5000 Rad) for 7 days in the presence of recombinant human IL-2 20 U/ml, and then collected as CTL effector cells. The NK activity and CTL activity were determined by a standard 4-h $^{51}Cr$ release assay. Two million YAC-1 or E.G7 thymoma cells in 0.5 ml RPMI-1640 with 20% FCS were labeled with 200 μCi $Na^{51}CrO_4$ (Amersham, Arlington Heights, USA). The labeled cells were washed three times in serum-free medium. Ten thousands of target cells were then mixed with effector cells in U-bottomed microwells for 4 h at 37° C. at the ratio indicated. For the maximal $^{51}Cr$ release control, 0.1 ml of 0.1 N HCl was added to the target cells, and for the spontaneous $^{51}Cr$ control, 0.1 ml of medium was added to the labeled cells. The amount of $^{51}Cr$ released was determined by γ counting on a 1275 Minigamma Counter (LKB-Wallac, Finland), and the percentage of lysis was calculated as follows:

NK or CTL activity (%)=(Experimental cpm−spontaneous cpm)/(Maximal cpm−spontaneous cpm)×100.

Example 11

Macrophage Cytotoxicity and NO Release Assay

The splenocytes were cultured in RPMI-1640 medium for 2 h and the adherent cells were collected as macrophages. For macrophage cytotoxicity assay, the adherent macrophages were incubated with L1210 cells at an effector: target ratio of 10:1 or 20:1 in a total volume of 0.1 ml medium per well in 96-well U-bottomed plate. After 20 h of co-incubation at 37° C., 5% $CO_2$ and 95% relative humidity, 10 ul MTT was added to L1210 cells transferred from macrophage-L1210 cultures. The L1210 cells were then incubated for 4 h in the presence of MTT followed by addition of 0.1 ml of 10% SDS in 0.01 N HCl. The formazan crystals were dissolved in 10% SDS and the absorbance was read at 540 nm on a BIO-RAD model 2550 microplate reader. Percentage of cytotoxicity was calculated relative to the calibration standard L1210 as follows:

percentage of cytotoxicity=$1-A_{L1210\ remained}/A_{L1210\ standard}$.

To determine the release of nitric oxide (NO) from macrophages, the macrophages, in the presence or absence of NO synthase inhibitor $N_{omega}$-nitro-1-arginine methyl ester (L-NAME) 1 μM, were stimulated with 10 ug/ml of LPS for 24 h at 37° C., 5% $CO_2$. The NO contents in the supernatants were determined using Griess' reagent (19).

Example 12

Cytokine Release Assay

The non-adherent splenocytes at a concentration of $2\times10^6$ cells/ml were stimulated with irradiated E.G7 cells (5000 Rad) at a ratio of 10:1. Supernatants were harvested after 24 h (for IL-2 assay), 48 h (for IL-4 and IFN-γ assay), or 72 h (for IL-10 assay). The cytokines were assayed using ELISA assay with corresponding kits from Endogen, Woburn, Mass., USA.

Statistics

All experiments were run in triplicate and the results were means ± SD of triplicate determinations or representative data of three independent experiments. The differences in tumor mean volume between treatment groups at each time points were compared using the independent t test. The differences in survival periods of the mice after various immunizations were compared using log-rank tests. Other statistical analyses were performed using the Student's t test. A P<0.05 was considered to be statistically significant.

RESULTS

Generation of H-2K$^b$/OVA$_{257-264}$ Tetramer

Monomeric MHC-peptide complexes had been used to identify the antigen-specific T cells, but the low affinity and high dissociation rate of the interaction between the complexes and T cell receptor made it impossible for the antigen-specific T cells to be identified. To increase the binding affinity, tetrameric MHC-peptide complexes were constructed by using biotin-avidin conjugation as a bridge, and were successfully used to stain the MHC-I- and MHC-II-restricted T cell subsets (20,21,22). In the invention, the plasmid harboring truncated extra-membrane H-2K$^b$ gene fused with cDNA encoding specific biotinylation site at the COOH end was constructed. After biotinylation and tetramerization, the specificity of the staining of the H-2K$^b$/OVA$_{257-264}$ tetramer was tested utilizing H-2Kb-restricted CD8+T cell hybridoma RF33.70 which was reactive with OVA$_{257-264}$ or CTL clone reactive with TRP2$_{180-188}$.

Figure 1:
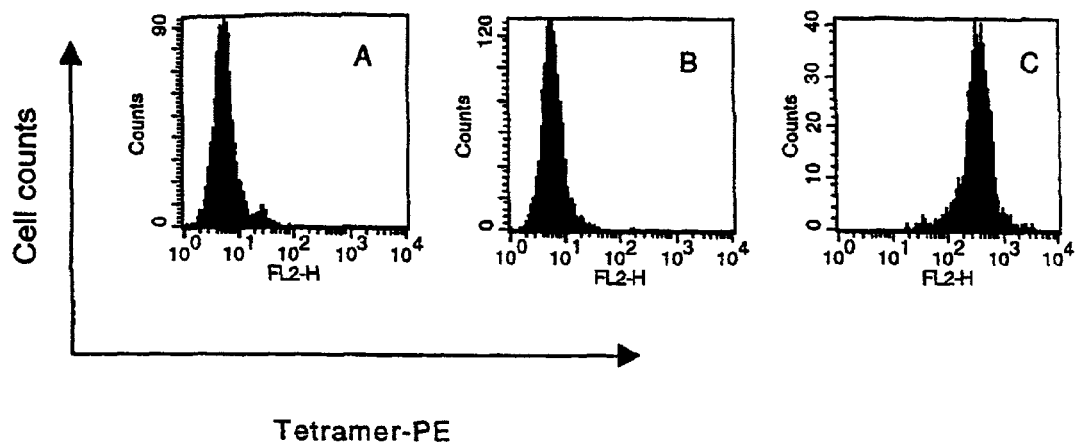
FIG. 1. Specificity of H-2K$^b$/OVA$_{257-264}$ tetramer. H-2K$^b$/OVA$_{257-264}$ tetramers were used for the staining of OVA$_{257-264}$ specific CTL hybridoma RF33.70 and TRP2$_{180-188}$ specific CTL clone, respectively. A, control cells without staining. B, TRP2 CTL clone stained with H-2K$^b$/OVA$_{257-264}$ tetramer. C, RF33.70 stained with H-2K$^b$/OVA$_{257-264}$ tetramer.

As shown in FIG. 1, there is a significant binding of H-2K$^b$/OVA$_{257-264}$ tetramer to OVA$_{257-264}$ specific T cell hybridoma RF33.70, but there is no binding of H-2K$^b$/OVA$_{257-264}$ tetramer to CTL clone which is reactive with TRP2$_{180-188}$.

Figure 2:
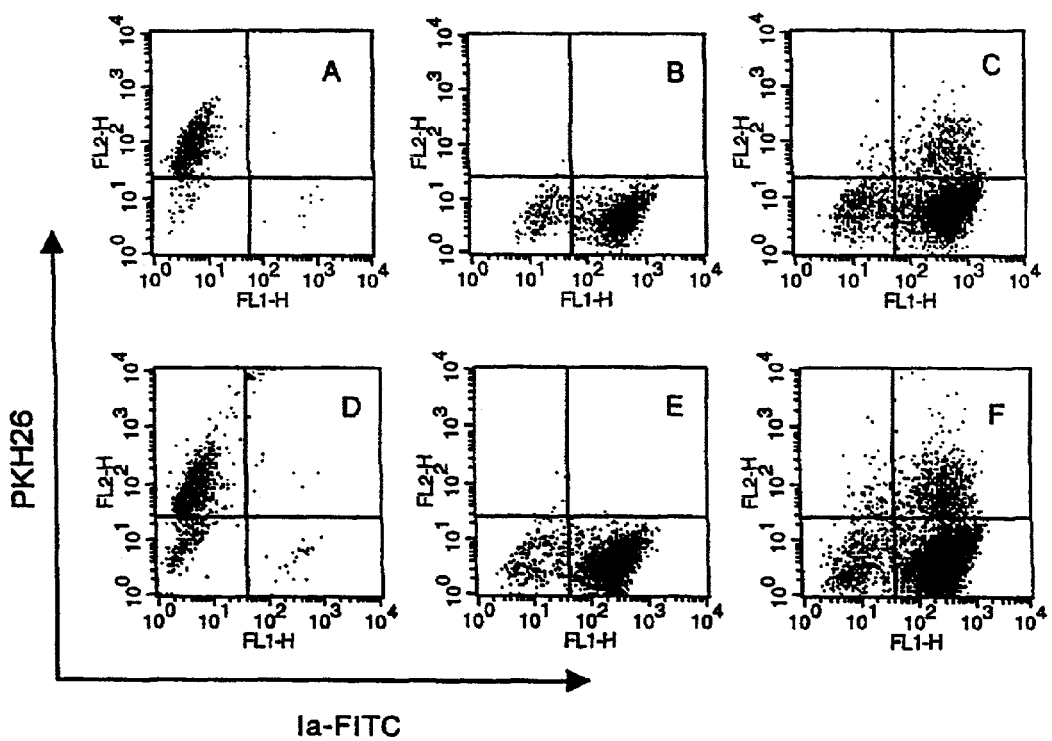
FIG. 2. Cell association between DC and E.G7 cells. PKH26-labeled E.G7 cells were incubated with DC at a ratio of 1:6 for 6 h (upper panel) and 24 h (below panel) and then stained with FITC-conjugated Ia$^b$ McAb for flow cytometry. A, D, E.G7 cells labeled with PKH26. B, E, DC labeled with FITC-conjugated Ia$^b$ McAb. C, DC-E.G7 conjugate after 6 h of incubation. F, DC-E.G7 conjugate after 24 h of incubation.

Immunization of Naive Mice with DC-E.G7 Vaccine Elicited Potent Antitumor Immunity To explore the immunogenicity of the non-fused DC-tumor cell conjugates, DC-E.G7 vaccine was first prepared by incubating these cells together with a ratio of 6:1 as reported elsewhere (Celluzzi CM, 1998, supra). The results in FIG. 2 demonstrated that the red dye PKH26 could label the tumor cell E.G7 efficiently, and FITC-conjugated Ia$^b$ antibody was used to label DC. After the labeled E.G7 and DC were co-cultured for 6 h and 24 h, the E.G7 cells were found to bind to the DC, and this interaction could not be affected after washing twice with PBS supplemented with 2% FCS, indicating stable cell association between tumor cells and DC.

Figure 3A:
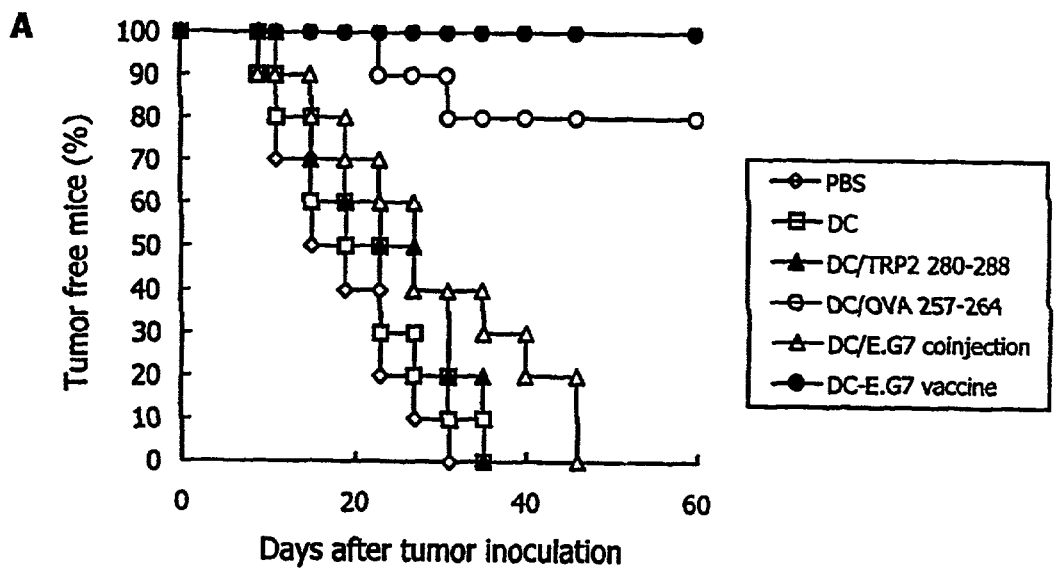
FIG. 3. Tumor protection induced by immunization with DC-E.G7 vaccine.
Figure 3B:
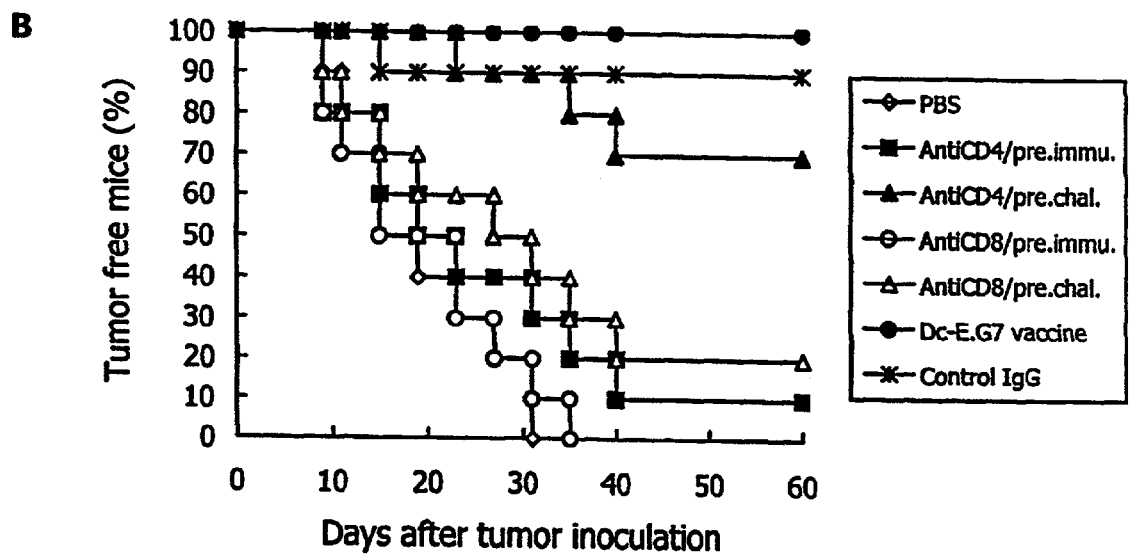

Then the syngenic naive C57BL/6 mice were immunized with the irradiated DC-E.G7 vaccine twice with 1-week interval. Seven days after immunization, the mice were challenged with E.G7 tumor cells. The results in FIG. 3A illustrated that all mice immunized with the DC-E.G7 vaccine remained tumor-free 3 months after the tumor challenge. As controls, the mice immunized with OVA$_{257-264}$-pulsed DC also showed obvious protection against the following tumor challenge, with 90% of the mice being tumor-free. The mice immunized with PBS, DC alone, DC pulsed with irrelevant peptide TRP2$_{180-188}$, or DC in combination with E.G7 without incubation showed no significant protection against the challenge by E.G7 cells. When CD4$^+$ T cells were depleted before immunization of the mice with DC-E.G7 vaccine, the protective effects of DC-E.G7 vaccine were almost completely eliminated. The protective effects of DC-E.G7 vaccine were also partially eliminated when CD4+T cells were depleted after immunization, indicating that CD4$^+$ T cells play an important role not only in the priming phase of the antitumor immunity but also in the effector phase of the antitumor response. Deletion of CD8$^+$ T cells either before immunization or before tumor challenging significantly eliminated the protective effects of DC-E.G7 vaccine, thus indicating the primary role of CD8$^+$ T cells in the antitumor immunity of the DC-E.G7 vaccine both in the priming phase and in the effector phase(FIG. 3B). These data strongly implicated the definite roles of both CD4$^+$ and CD8$^+$ T cells in the antitumor immunity induced by the DC-E.G7 vaccine.

Figure 3C:
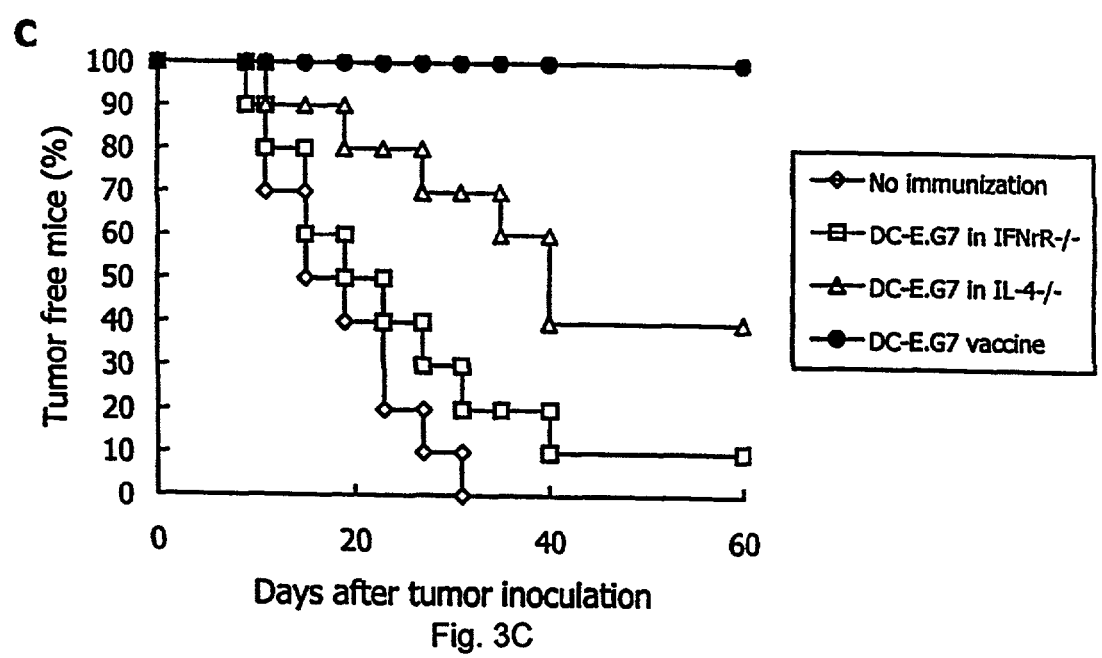

To further determine the mechanisms underlying the antitumor immunity of the CD4$^+$ T cells, IFN-γ-R$^{-/-}$ and IL-4-deficient mice were used to demonstrate the roles of endogenous Th1 and Th2 cytokines in the antitumor process of DC-tumor vaccine. The data in FIG. 3C showed that, in IFN-γ-R$^{-/-}$ mice, the protective effects of DC-E.G7 was almost completely eliminated, indicating IFN-γ-mediated Th1 response was required for the induction of antitumor immunity. But unexpectedly, in IL-4$^{-/-}$ mice, the protective effects of DC-E.G7 vaccine were also partially eliminated, suggesting the important role of endogenous IL-4 in the induction of antitumor response.

Induction of Tumor Specific CD8$^+$ T Cells

Tumor specific CTL play key roles in the antitumor immunity of tumor vaccines. Peptide/MHC-I tetramer has been proved to be efficient approach to the direct detection of antigen-specific T cells after viral infection. Usage of tetramer to stain tumor antigen-specific T cells in patients was reported only recently (23). In the invention, the non-adherent lymphocytes were stained with H-2K$^b$/OVA$_{257-264}$ tetramer. The results in FIG. 4 A-F demonstrated that after immunization with either OVA$_{257-264}$-pulsed DC or DC-E.G7 vaccine, significant tetramer$^+$ CD8$^+$ T cells were induced, which were about 3-7 percent of the splenic CD8$^+$ T cells. No tetramer$^+$ CD8$^+$ T cells were found in lymphocytes derived from mice immunized with PBS, or DC pulsed with control peptide TRP2$_{180-188}$. The induction of antigen-specific CTL was significantly impaired in IFN-γ-R gene- or IL-4 gene-deficient mice immunized with DC-E.G7 vaccine, indicating that both endogenous Th1 and Th2 cytokines were required for the induction of antitumor CTL in mice immunized with DC-tumor vaccine. Then, the specific lytic activity of lymphocytes from the mice after various immunizations was determined. It was found that (FIG. 4G) the cytotoxicity of the lymphocytes had a positive correlation with the results of tetramer staining. The lymphocytes from mice immunized with DC-E.G7 vaccine or OVA$_{257-264}$-pulsed DC showed significant lytic activity against E.G7 cells. In contrast, the lymphocytes derived from mice after control immunizations and those in IFN-γ-R$^{-/-}$, IL-4$^{-/-}$ mice showed no obvious lytic activity against target E.G7 cells. These lymphocytes showed little lytic activity on syngenic B16 melanoma cells, indicating that the lytic activity was contributed by tumor antigen-specific CTL.

These data illustrated that immunization of mice with DC-E.G7 vaccine could elicit potent protective antitumor immunity. DC-tumor cell association was necessary for the immunogenicity of the conjugate vaccine. Th1, Th2, CD4$^+$ T cells and CD8$^+$ T cells were involved in the induction of antitumor immunity by DC-E.G7 vaccine.

Figure 5A:
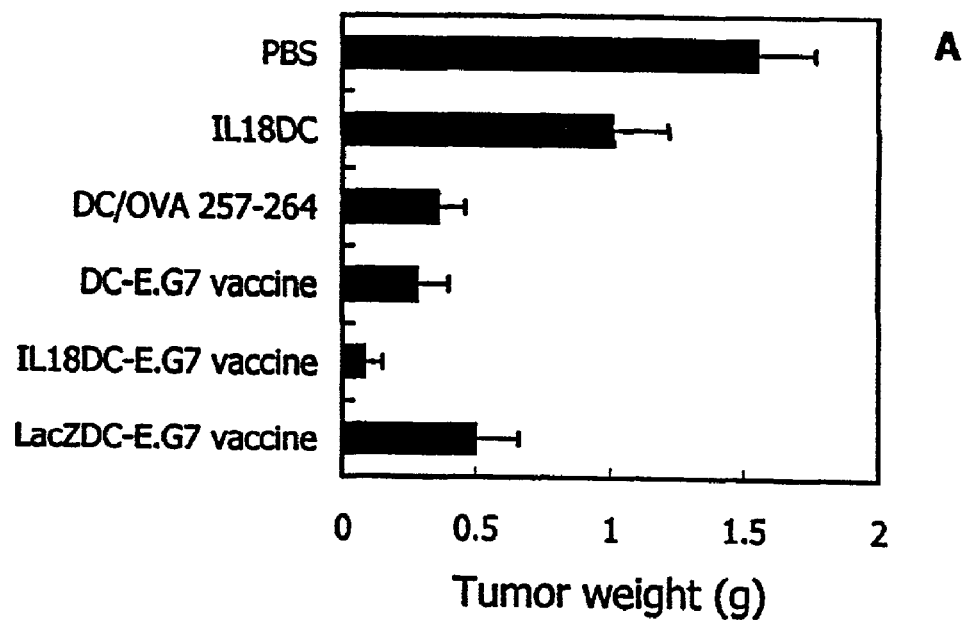

More Potent Antitumor Effects of IL-18-secreting DC-E.G7 Vaccine on Established Tumors Since CD4$^+$ cells play important roles in the induction of antitumor immunity, anti-tumor immunity is often mediated by CTL, and Th1 cytokines play crucial roles in the activation of CTL, we hypothesized that increasing the T helper effects might be of great merit to enhance the antitumor response and the induction of antitumor immunity in a DC-based immunotherapy of established tumors. So Th1 cytokine IL-18 was chosen. Adenovirus harboring murine IL-18 gene was transferred into DC at a MOI of 10:1 before the preparation of DC-E.G7 vaccine. One hundred thousand of E.G7 cells were inoculated s. c. into wild type C57BL/6 mice, IFN-γ-R-/- or IL-4$^{-/-}$ mice. Three days later these mice were treated with the following preparations: IL-18 gene- or control Lac Z gene-modified DC-E.G7 vaccine, DC-E.G7 vaccine, OVA$_{257-264}$ pulsed DC, IL-18-gene modified DC alone, or PBS. The same injections were repeated 7 days later and the tumor-bearing mice were sacrificed after another 7 days for evaluation of tumor weight or determination of antitumor immunity. As shown in FIG. 5A the results demonstrated that in pre-established tumor model, the tumor growth in mice treated with LacZ gene-modified DC-E.G7 vaccine, DC-E.G7 vaccine, or OVA$_{257-264}$ pulsed DC was significantly inhibited when compared with that in mice treated with PBS ($P<0.05$). More potent antitumor effect was observed in mice treated with IL-18 gene-modified DC-E.G7 vaccine when compared with the mice treated with lacZ gene-modified DC-E.G7 vaccine, DC-E.G7 vaccine, or OVA$_{257-264}$ peptide pulsed DC ($P<0.05$). Immunotherapy with DC transfected with AdIL18 also showed therapeutic effects on the established E.G7 tumors, whose effects might be elicited through the IL-18 secreted by DC. The surviving tumor-free mice were re-challenged with wild E.G7 cells, and 5 of 5 mice treated with IL18DC-E.G7 were tumor free after another 3 months, suggesting that potent antitumor immunity was induced in IL18DC-E.G7 vaccine treated mice (Table 1).

TABLE 1

Tumor free mice treated with IL-18 gene-modified DC-E.G7 vaccine and followed by re-challenging with wild type E.G7 cells.

| Groups | Tumor free mice[a] | Tumor free mice[b] |
|---|---|---|
| IL18DC-E.G7 vaccine | 9/10 | 5/5 |
| LacZDC-E.G7 vaccine | 5/10 | 2/5 |
| DC-E.G7 vaccine | 4/10 | |
| DC/OVA 257–264 | 6/10 | 3/5 |
| IL18DC | 2/10 | |
| DC | 1/10 | |
| PBS | 0/10 | |
| Naive mice[c] | | 0/5 |

[a]Tumor free mice 3 months after tumor inoculation
[b]Tumor free mice after IL-18 gene-modified DC-E.G7 vaccine were re-challenged with wild type 10$^5$ E.G7 cells and data demonstrating tumor-free mice after another 3 months.
[c]Naive mice receive neither tumor inoculation nor immunotherapy. These mice were challenged with E.G7 cells as control.

Figure 5B:
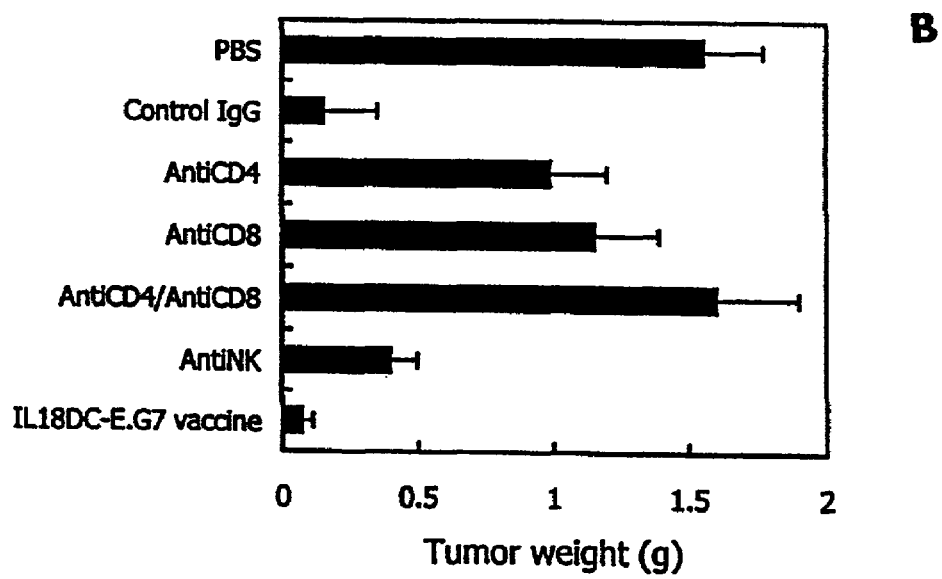

Anti-CD4, anti-CD8 and anti-NK1.1 antibodies were injected 4, 1 days before and 2, 5, 8 days after tumor inoculation to determine the cell subsets responsible for the increased antitumor effects of IL-18 gene-modified DC-E.G7 vaccine. The results in FIG. 5B showed that both CD4$^+$ T and CD8$^+$ T cell depletion blocked the therapeutic effects of IL18DC-E.G7 vaccine by 60–80%. Complete loss of antitumor efficacy of IL18DC-E.G7 vaccine was observed in mice treated with both anti-CD4 and anti-CD8 antibodies when compared with the mice received no immunotherapy. Interestingly, treatment of the mice undergoing immunotherapy with anti-NK1.1 antibody also partially blocked the antitumor effects of IL18DC-E.G7 vaccine. To explain the role of NK in the antitumor response, the expression of H-2K$^b$ was determined by flow cytometry, and high expression of H-2K$^b$ was observed with the E.G7 cells (data not shown). MHC-I expressing tumor cells are resistant to the lysis of NK cells by the induction of inhibitory NK receptors (24). The lymphokines produced after IL-18 gene-modification might activate the NK cells, and the lymphokine-activated NK cells were speculated to be involved in the antitumor effects of the IL18DC-E.G7 vaccine.

Figure 5C:
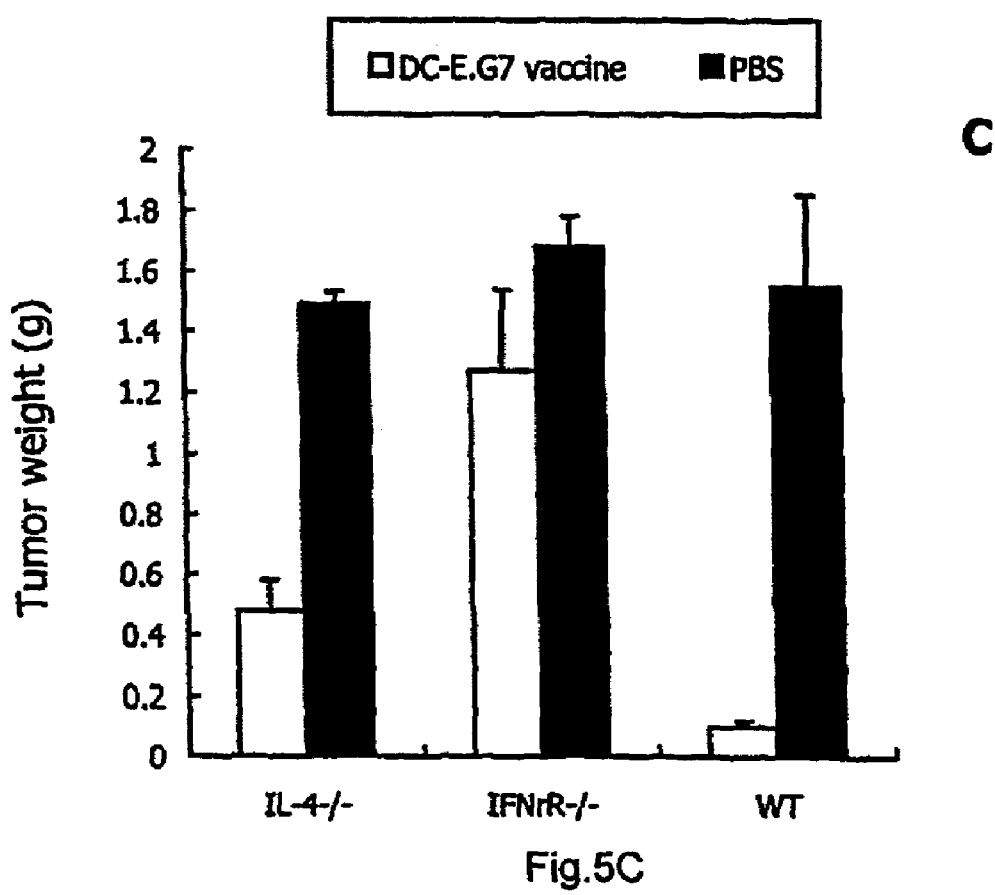

The E.G7 tumors growing in wild type C57BL/6 mice, IFN-γ-R$^{-/-}$ and IL-4$^{-/-}$ mice showed no differences (FIG. 5C). Identical tumor growth between IL-4$^{++}$ and IL-4$^{-/-}$ mice was also reported recently (25). But when these established tumors in these mice were treated with IL-18DC-E.G7 vaccine, it was found that in IFN-γ-R$^{-/-}$ mice, almost no therapeutic antitumor was observed. Although antitumor effects were observed in IL-4$^{-/-}$ mice, these tumors in IL-4$^{-/-}$ mice were significantly larger than those in wild type mice, indicating the crucial role of IFN-γ and participation of endogenous IL-4 in the antitumor response of IL-18 gene-modified DC-tumor vaccine.

Induction of Antigen-Specific CD8$^+$ T Cells by Treating with IL18DC-E.G7 Vaccine To determine if the IL-18 gene-modified DC-E.G7 induced more tumor-specific CD8$^+$ T cells in mice with pre-established tumors, H-2K$^b$/OVA$_{257-264}$ tetramer was utilized to stain the lymphocytes 7 days after immunotherapy. The results in FIG. 6 A-F demonstrated that there were more OVA-specific CD8$^+$ tetramer$^+$ T cells in mice treated with IL18DC-E.G7 vaccine as compared with that in mice treated with DC-E.G7 vaccine, OVA$_{257-264}$ pulsed DC, or PBS. The percentages of CD8$^+$ tetramer$^+$ T cells in mice after immunotherapy with either DC-E.G7 vaccine or OVA$_{257-264}$ pulsed DC were also significantly higher than those after PBS therapy, which is consistent with results obtained with DC-E.G7 immunization. The numbers of CD8$^+$ tetramer$^+$ T cells in IFN-γ-R$^{-/-}$ and IL-4$^{-/-}$ mice receiving immunotherapy with IL18DC-E.G7 vaccine were significantly lower than those in normal C57BL/6 mice. The specific lysis of lymphocytes after in vitro stimulation by irradiated E.G7 cells were assayed by 4 h $^{51}$Cr releasing method. As shown in FIG. 6 G, much higher CTL activity was observed in mice treated with IL18DC-E.G7 vaccine as compared with that in mice treated with DC-E.G7 vaccine, OVA$_{257-264}$ pulsed DC, or PBS ($P<0.05$). The CTL activities in mice after immunotherapy with either DC-E.G7 vaccine or OVA$_{257-264}$ pulsed DC were significantly higher than those after PBS treatment ($P<0.01$). CTL induction was almost completely eliminated in IFN-γ-R$^{-/-}$ and IL-4$^{-/-}$ mice receiving immunotherapy with IL18DC-E.G7 vaccine. These data suggested that both IFN-γ and IL-4 played crucial roles in the augmented activation of OVA-specific CD8$^+$ T cells after immunotherapy with IL18 DC-E.G7 vaccine.

Cytokine Production by Splenic Lymphocytes Derived from Tumor-Bearing Mice after Immunotherapy with IL18DC-E.G7 Vaccine Erythrocyte-depleted, non-adherent lymphocytes were stimulated in vitro with irradiated E.G7 cells for the induction of Th1 and Th2 cytokines. The results in FIG. 7A and B demonstrated that the production of IL-2 and IFN-γ from lymphocytes derived from mice treated with IL18DC-E.G7 vaccine was significantly higher than that from mice treated with DC-E.G7 vaccine, OVA$_{257-264}$ pulsed DC, or PBS (P<0.01). After IL18DC-E.G7 vaccine immunotherapy, the lymphocytes in IFN-γ-R$^{-/-}$ and IL-4$^{-/-}$ mice produced significantly less amounts of IL-2 and IFN-γ as compared with those in normal mice (P<0.05). A little IL-2 and no IFN-γ contents were detected in the supernatants of the lymphocytes derived from mice mock-treated with PBS, indicating that the Th1 cytokines release after E.G7 stimulation was antigen-specific. The production of IL-4 and IL-10 by lymphocytes from mice after various treatments was also determined and the results in FIG. 7C and D demonstrated that the production of IL-4 was in a similar pattern with that of IL-2 and IFN-γ. IL-10 production by lymphocytes was not significantly influenced by the immunotherapy of the tumor-bearing mice with DC-E.G7 vaccine or peptide pulsed DC, indicating that IL-4 and IL-10 might have diverse roles in the antitumor immunity of the IL-18DC-E.G7 vaccine.

Activation of NK Cells in Tumor-Bearing Mice after Immunotherapy with IL18DC-E.G7 Vaccine One of the mechanisms involved in the anti-viral and antitumor effects of CD4$^+$ T cells is mainly through the activation of non-specific effector cells such as NK cells, macrophages, neutrophils and eosinophils. These effector cells, whose activation was dependent on the Th1 cytokine IL-2, IFN-γ, or Th2 cytokine IL-4, IL-5, could kill target cells efficiently. In this study, after we observed that CD4$^+$ T cells participated in the effector phase of antitumor immunity of the conjugate vaccine, we investigated the roles of NK and macrophages in the augmented antitumor response of the IL18DC-E.G7 vaccine.

The results in FIG. 8A showed that the NK activity of lymphocytes derived from mice after immunotherapy with IL18DC-E.G7 vaccine was much higher as compared with those from mice after immunotherapy with DC-E.G7 vaccine, OVA$_{257-264}$ pulsed DC or PBS (P<0.01). The NK cell activity derived from mice treated with DC-E.G7 vaccine without IL-18 transduction was higher than that in mice treated with OVA$_{257-264}$ pulsed DC. In IFN-γ-R$^{-/-}$ mice treated with IL18DC-E.G7 vaccine, the NK activity was significantly lower than that in wild type C57BL/6 mice (P<0.05). But, in IL-4$^{-/-}$ mice, the NK activity after IL18DC-E.G7 vaccine was almost the same as that from normal mice. These data indicated that the increased NK activity in mice treated with DC-E.G7 vaccine might be due to the activation of CD4$^+$ T cells in the effector phase of antitumor response.

Enhanced Cytotoxicity and NO Production of Macrophages in Tumor-Bearing Mice after Immunotherapy with IL18DC-E.G7 Vaccine As shown in FIG. 8B, the cytotoxicities of splenic macrophages derived from mice treated with IL18DC-E.G7 vaccine were markedly higher than those from mice treated with other DC-based vaccine and PBS (P<0.01). In mice depleted of CD4$^+$ T cells by injection of anti-CD4$^+$ antibody, no increased NK and macrophage cytotoxicity was observed in tumor-bearing mice treated with IL18DC-E.G7 vaccine. When comparing the NK activity and macrophage cytotoxicity between mice treated with DC-E.G7 vaccine and OVA$_{257-264}$ pulsed DC, it was found that these lytic activities from DC-E.G7 vaccine-treated mice was higher than mice treated with OVA$_{257-264}$ pulsed DC, thus suggesting that DC-E.G7 vaccine could induce CD4$^+$ T cell activation while OVA$_{257-264}$ pulsed DC therapy could not. Since IL-18 was a potent inducer of IFN-γ, which was reported to exhibit tumor cell lysing effect through the production of NO by macrophages (2), we also determined the production of NO by macrophages. The results showed that NO production was correlated positively with the macrophage activity. NO synthase inhibitor L-NAME significantly eliminated the cytotoxicity and production of NO of macrophages, indicating that the macrophages might elicit lytic effects on tumor cells through the production of NO.

All the documents cited herein are incorporated into the invention as reference, as if each of them is individually incorporated. Further, it is appreciated that, in the above teaching of the invention, the skilled in the art can make certain changes or modifications to the invention, and these equivalents are still within the scope of the invention defined by the appended claims of the present application.

REFERENCE

1. Pardoll, D. M. Therapeutic vaccination for cancer. Clin. Immunol., 95:S44–62, 2000.
2. Xie K, Bielenberg D, Huang S, Xu L, Salas T, Juang S H, Dong Z, Fidler I J. Abrogation of tumorigenicity and metastasis of murine and human tumor cells by transfection with the murine IFN gene: possible role of nitric oxide. Clin Cancer Res 1997;3:2283–2294
3. Fong, L., and Engleman, E. G. Dendritic cells in cancer immunotherapy. Annu. Rev. Immunol., 18: 245–273, 2000.
4. Flamand, V., Somasse, T., Thielemans, K., Demanet, C., Bakkus, M., Bazin, H., Tielemans, F., Leo, O., Urbain, J., and Moser, M. Murine dendritic cells pulsed in vitro with tumor antigen induce tumor resistance in vivo. Eur. J. Immunol., 24: 605–610, 1994.;
5. Celluzzi, C. M., Mayordomo, J. I., Storkus, W. J., Lotze, M. T., and Falo, L. D. Jr. Peptide-pulsed dendritic cells induce antigen-specific CTL-mediated protective tumor immunity. J. Exp. Med., 183: 283–287.1996.
6. Fields, R. C., Shimizu, K., and Mule, J. J. Murine dendritic cells pulsed with whole tumor lysates mediate potent antitumor immune responses in vitro and in vivo. Proc. Natl. Acad. Sci. U. S. A., 95: 9482–9487, 1998.;
7. Boczkowski, D., Nair, S. K., Nam, J. H., Lyerly, H. K., and Gilboa, E. Induction of tumor immunity and cytotoxic T lymphocyte responses using dendritic cells transfected with messenger RNA amplified from tumor cells. Cancer Res., 60: 1028–1034, 2000.
8. Micallef, M. J., Yoshida, K., Kawai, S., Hanaya, T., Kohno, K., Arai, S., Tanimoto, T., Torigoe, K., Fujii, M., Ikeda, M., and Kurimoto, M. In vivo antitumor effects of murine interferon-gamma-inducing factor/interleukin-18 in mice bearing syngeneic Meth A sarcoma malignant ascites. Cancer Immunol. Immunother., 43: 361–367, 1997.;
9. Osaki, T., Peron, J. M., Cai, Q., Okamura, H., Robbins, P. D., Kurimoto, M., Lotze, M. T., and Tahara, H. IFN-gamma-inducing factor/IL-18 administration mediates IFN-gamma- and IL-12-independent antitumor effects. J. Immunol., 160: 1742–1749, 1998.
10. Nakamura, S., Otani, T., Ijiri, Y., Motoda, R., Kurimoto, M., and Orita, K. IFN-gamma-dependent and -independent mechanisms in adverse effects caused by concomitant administration of IL-18 and IL-12. J. Immunol., 164: 3330–3336, 2000.
11. Coughlin, C. M., Salhany, K. E., Wysocka, M., Aruga, E., Kurzawa, H., Chang, A. E., Hunter, C. A., Fox, J. C., Trinchieri, G., and Lee, W. M. F. Interleukin-12 and interleukin-18 synergistically induce murine tumor regression which involves inhibition of angiogenesis. J. Clin. Invest., 101: 1441–1452, 1998.
12. Schatz P J. Use of peptide libraries to map the substrate specificity of a peptide-modifying enzyme: a 13 residue consensus peptide specifies biotinylation in *Escherichia coli*. Biotechnology (N Y) 1993,11:1138–1143;
13. Altman J D, Moss P A H, Goulder P J R, Barouch D H, McHeyzer-Williams M G, Bell J I, McMichael A J, Davis M M. Phenotypic analysis of antigen-specific T lymphocytes. Science 1996;274 :94–96.
14. Celluzzi C M, Mayordomo J I, Storkus W J, Lotze M T, Falo L D Jr. Peptide-pulsed dendritic cells induce antigen-specific CTL-mediated protective tumor immunity. J Exp Med 1996;183:283–287;
15. Bloom M B, Perry-Lalley D, Robbins P F, Li Y, el-Gamil M, Rosenberg S A, Yang J C. Identification of tyrosinase-related protein 2 as a tumor rejection antigen for the B16 melanoma. J Exp Med 1997;185:453–459
16. Kanai F, Lan K H, Shiratori Y, Tanaka T, Ohashi M, Okudaira T, Yoshida Y, Wakimoto H, Hamada H, Nakabayashi H, Tamaoki T, Omata M. In vivo gene therapy for alpha fetoprotein producing hepatocellular carcinoma by adenovirus mediated transfer of cytosine deaminase gene. Cancer Res 1997;57:461–465
17. Specht J M, Wang G, Do M T, Lam J S, Royal R E, Reeves M E, Rosenberg S A, Hwu P. Dendritic cells retrovirally transduced with a model antigen gene are therapeutically effective against established pulmonary metastases. J Exp Med 1997;186:1213–1221
18. Celluzzi C M, Falo L D Jr. Cutting Edge: Physical interaction between dendritic cells and tumor cells results in an immunogen that induces protective and therapeutic tumor rejection. J Immunol 1998;160:3081–3085
19. Amano F, Noda T. Improved detection of nitric oxide radical (NO.) production in an activated macrophage culture with a radical scavenger, carboxy PTIO and Griess reagent. FEBS Lett 1995;368:425–458
20. Gutgemann I, Fahrer A M, Altman J D, Davis M M, Chien Y H. Induction of rapid T cell activation and tolerance by systemic presentation of an orally administered antigen. Immunity 1998;8:667–673;
21. Gray C M, Lawrence J, Schapiro J M, Altman J D, Winters M A, Crompton M, Loi M, Kundu S K, Davis M M, Merigan T C. Frequency of class I HLA-restricted anti-HIV CD8[+] T cells in individuals receiving highly active antiretroviral therapy (HAART). J Immunol 1999; 162:1780–1788;
22. Seth A, Ourmanov I, Kuroda M J, Schmitz J E, Carroll M W, Wyatt L S, Moss B, Forman M A, Hirsch V M, Letvin N L. Recombinant modified vaccinia virus Ankarasimian immunodeficiency virus gag pol elicits cytotoxic T lymphocytes in rhesus monkeys detected by a major histocompatibility complex class I/peptide tetramer. Proc Natl Acad Sci U S A 1998;95:10112–10116
23. Yee C, Savage P A, Lee P P, Davis M M, Greenberg P D. Isolation of high avidity melanoma-reactive CTL from heterogeneous populations using peptide-MHC tetramers. J Immunol 1999;162:2227–2234
24. Sundback J, Nakamura M C, Waldenstrom M, Niemi E C, Seaman W E, Ryan J C, Karre K. The alpha2 domain of H-2Dd restricts the allelic specificity of the murine NK cell inhibitory receptor Ly-49A. J Immunol 1998;160: 5971–5978
25. Schuler T et al., T helper cell type 1-associated and cytotoxic T lymphocyte-mediated tumor immunity is impaired in interleukin 4-deficient mice, Exp Med 189: 803–810, 1999

The invention claimed is:

1. An autoloaous antigen-presenting cell-autologous tumor cell conjugate, wherein the autologous antigen-presenting cell (APC) is modified by a polynucleotide encoding and expressing IL-18.

2. The conjugate of claim 1, wherein said APC is selected from the group consisting of dendritic cell, macrophage, B cell, endothelial cell, Langerhans cell, and the combination thereof.

3. The conjugate of claim 1, wherein said tumor cell is selected from the group consisting of a fresh tumor cell isolated from a tumor tissue and a tumor cell line cultured in vitro.

4. The conjugate of claim 1, wherein said tumor cell is selected from the group consisting of the cell of melanoma, kidney cancer, pulmonary carcinoma, hepatic carcinoma, mammary cancer, prostatic carcinoma, gastric carcinoma, and leukemia.

5. The conjugate of claim 1, wherein the ratio of said APC to rumor cell is 100:1–0.1:1.

6. The conjugate of claim 1, wherein said conjugate is formed by incubating said APC with said tumor cell in a temperature range of 30–38° C. for 1–100 hrs.

7. A method for preparing an autologous antigen-presenting cell/autologous tumor cell conjugate, comprising the steps of:
 (1) providing an autologous antigen-presenting cell and an autologous tumor cell, wherein the autologous antigen-presenting cell is modified by a polynucleotide encoding and expressina IL-18;
 (2) incubating the APC and the tumor cell at a ratio of 100:1–0.1:1 in a temperature range of 30–38° for 1–100 hrs to form the antigen-presenting cell/tumor cell conjugate.

8. The method of claim 7, wherein the method further comprises the step of:
 (3) irradiating said conjugate with a dose of 1000–100,000 Rad or chemically inactivating the formed conjugate.

9. A pharmaceutical composition comprising the antigen-presenting cell/tumor cell conjugate of claim 1 and the pharmaceutically acceptable carrier or excipient or adjuvant.

10. The pharmaceutical composition of claim 9 wherein the composition is a tumor vaccine.

* * * * *

SEQUENCE LISTING

<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<221> NAME/KEY: misc_feature
<223> OTHER INFORMATION: Primer

<400> SEQUENCE: 1
ctagctagcg gcccacactc gctgagg         27

<210> SEQ ID NO 2
<211> LENGTH: 81
<212> TYPE: DNA
<213> ORGANISM: Artificial Sequence
<220> FEATURE:
<221> NAME/KEY: misc_feature
<223> OTHER INFORMATION: Primer

<400> SEQUENCE: 2
cgcggatcct taacgatgat tccacaccat tttctgtgca tccagaatat gatgcaggga         60
tccagtggat ggaggaggct c         81

<210> SEQ ID NO 3

```
-continued

<211> LENGTH: 8
<212> TYPE: PRT
<213> ORGANISM: Artificial Sequence
<220> FEATURE:
<221> NAME/KEY: MISC_FEATURE
<223> OTHER INFORMATION: amino acid sequence of OVA residues 257-264

<400> SEQUENCE: 3

Ser Ile Ile Asn Phe Glu Lys Leu
1               5

<210> SEQ ID NO 4
<211> LENGTH: 9
<212> TYPE: PRT
<213> ORGANISM: Artificial Sequence
<220> FEATURE:
<221> NAME/KEY: MISC_FEATURE
<223> OTHER INFORMATION: amino sequence of TRP2 residues 180-188

<400> SEQUENCE: 4

Ser Val Tyr Asp Phe Phe Val Trp Leu
1               5
```